United States Patent [19]

Bauer, deceased et al.

[11] Patent Number: Plant 5,918

[45] Date of Patent: Mar. 31, 1987

[54] VARIETY OF RIBES NIDIGROLARIA NAMED JOSTAKI

[75] Inventors: Rudolf Bauer, deceased, late of Breitbrunn, Fed. Rep. of Germany; *by Annelise Bauer, heir,* Hechistrasse 11, D-8211 Breitbrunn, Fed. Rep. of Germany

[73] Assignee: Annelise Bauer, Breitbrunn, Fed. Rep. of Germany

[21] Appl. No.: 701,183

[22] Filed: Feb. 13, 1985

[51] Int. Cl.[4] ..... A01H 5/00

[52] U.S. Cl. ..... Plt./33

[58] Field of Search ..... Plt./33

*Primary Examiner*—James R. Feyrer

*Attorney, Agent, or Firm*—Webb, Burden, Robinson & Webb

[57] ABSTRACT

A new F3 open pollinated selection between a black currant and a gooseberry is particularly distinguished by its large berry size. The new variety has the further characteristics of the variety *Ribes nidigrolaria.*

2 Drawing Figures

BACKGROUND OF THE PLANT

The present invention comprises a new and distinct variety of *Ribes nidigrolaria* known by the varietal name Jostaki.

The new variety was discovered in 1980 in a selective breeding program in the Federal Republic of Germany. The breeding took place in Koln-Vogelsang and the selection at Breitbrunn, Federal Republic of Germany. The new variety is an F3 open pollinated selection of Black currant—Variety "Schwarze Traube"-×Gooseberry—wild variety *Ribes divaricatum.* The botanical denomination used for the new species "*Ribes nidigrolaria*" is a neologism the creation of which is not yet officially known.

*Ribes nidigrolaria* are new amphidiploid species hybrids between black current (*Ribes nigrum*) and gooseberry (*Ribes grossularia*).

The new variety has been repeatedly asexually reproduced in the Federal Republic of Germany. It has been found to retain its distinctive characteristics through successive propagation.

Since 1948, crosses followed by polyploidization have been made between cultivars and wild species of black currant and gooseberry, to combine useful plant and resistance characteristics and high quality of berries. Selections have yielded amphidiploid breeding lines with desired combination or resistance to leaf fall diseases (*Pseudopeziza ribes* and *Cronartium ribicola*), mildew (*Sphaerotheca mors uvae*) with freedom from gall mites ("big bud").

Selfings of primary amphidiploids showed the expected complex heredity of growth and resistance characteristics. The fertility of F2-hybrids, however, was low.

By crossing induced tetraploid F1-hybrids of different origins, the effect of inbreeding depression was overcome. It was possible to obtain F2-hybrids with large fruits, high yielding capacity and sufficient self-fertility. Of those with the desired resistance combination, selection for future cultivars was started.

In 1977 the first cultivar of *Ribes nidigrolaria* was introduced under the name of Josta.

GENERAL DESCRIPTION OF *RIBES NIDIGROLARIA* HYBRIDS

Plant Character

*Ribes nidigrolaria* hybrids show heterosis in their growing characteristics. They are very vigorous. In growing capacity they exceed the cultivars of black currant and gooseberry. They are spinefree. In shape and size the leaves are between the parent species. They are tetraploid.

Flower and Fruit Characteristics

The flowers are larger than those of the parents. Fruit size is intermediate between black currants and gooseberries; the average number of berries per cluster is 3–4 berries. They are similar to gooseberries in the green pre-mature stage. At full maturity they reach the dark coloring of black currants. The hybrids do not have the characteristic "nidigrum" odor of black currant. They have no oil glands. The berries are predominantly oval-round. They flower and ripen in the same period as the original species.

Quality

At full maturity the berries combine the refreshing acidition and fine aroma of gooseberries with obvious participation of the flavor of black currants. The Vitamin C content reaches the level of black currants. The berries are particularly well-suited for making products of high quality, as well as for freezing.

Yield

Yield begins in the second year. The yield capacity is very high. In years with spring frost, the hybrids are as at risk as the parents.

Resistance

Leaves and shoots are fully resistant against leaf fall diseases, mildew and gall mites. Therefore, they are free from "big bud" and also free from virus diseases transmitted by gall mites.

Cultivation and Care

The plants require a growing space of about $4m^2$. They do not need to be trimmed the first years. Undisturbed, they reach a balance between vegetative and generative growth already in the third year which lasts a long time. The main branches are as long-lived as those of the gooseberry. They do not require a cut back for regeneration as black currants do. Due to their combined resistance they do not need spraying.

Recommendation

The new hybrids are conditionally recommended for commercial production. The berries are firmly attached to the plant and must be picked by hand. They are not suitable for mechanical harvesters. For the home garden they represent an ideal easy care plant which brings good yields.

Based on its inherent resistance against gall mites and leaf fall diseases, the hybrids of *Ribes nidigrolaria* are a good substitute for the cultivation of black currants which are losing their planting value due to their increasing infection caused by gall mites.

DESCRIPTION OF THE DRAWINGS

The accompanying photographic drawings illustrate the new variety, with color being as nearly true as color illustrations of this type.

DESCRIPTION OF THE NEW PLANT

Figure 1:
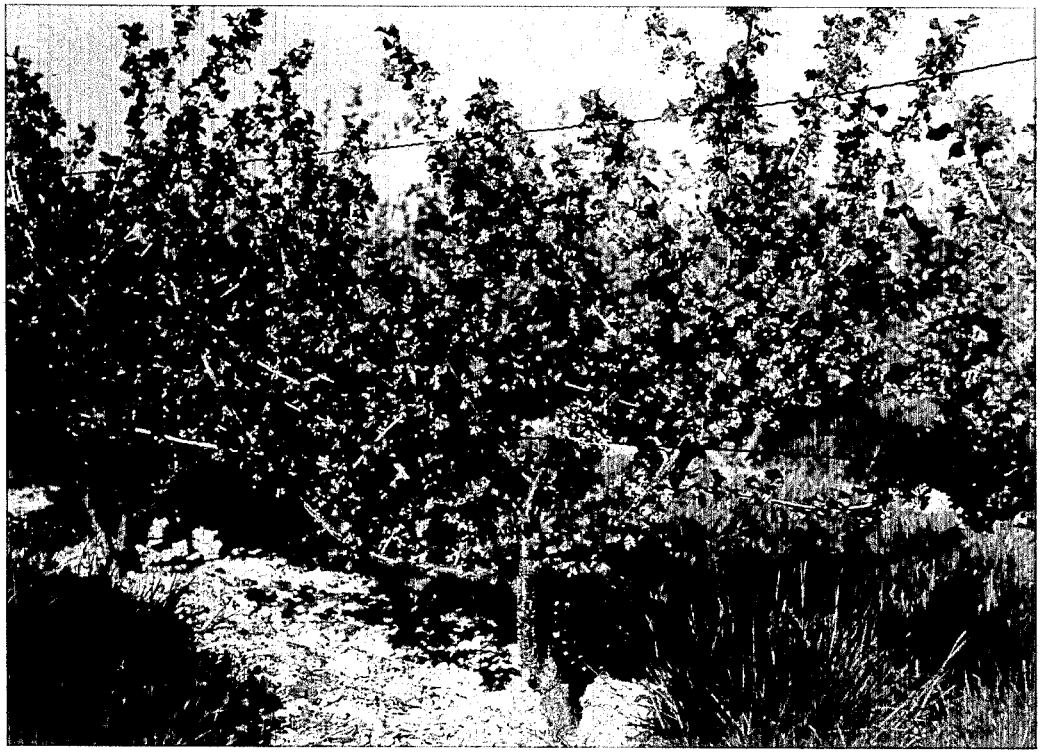
FIG. 1 is a photograph showing the new variety plant.
Figure 2:
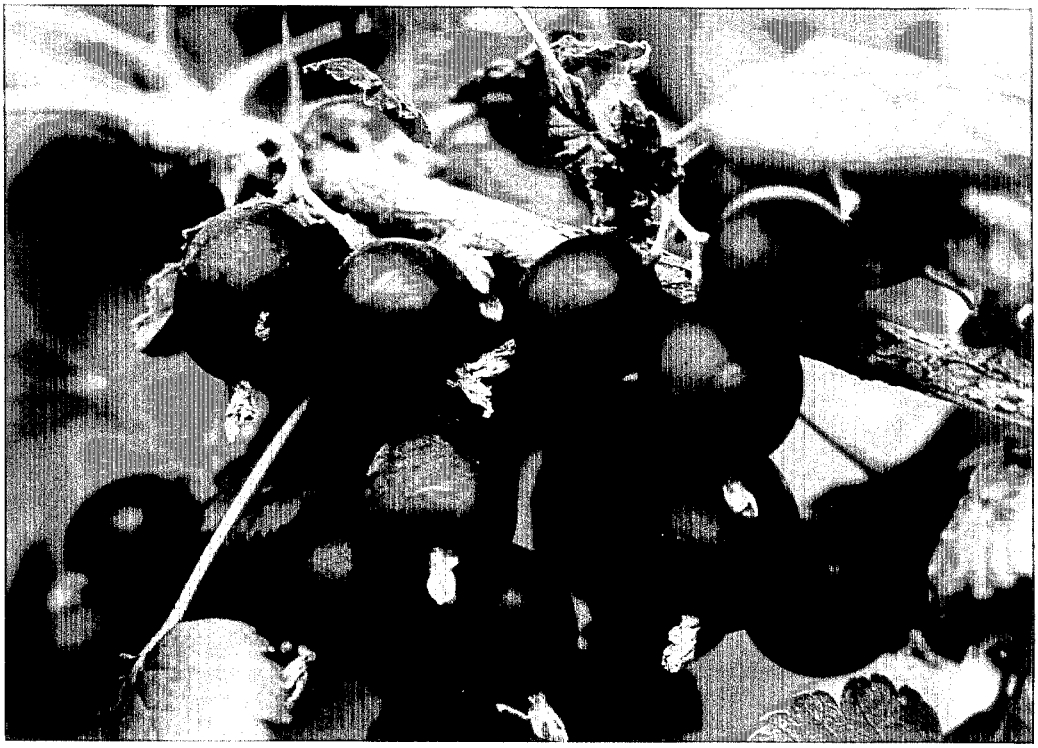
FIG. 2 is a photograph showing a close-up of the fruit clusters.

The variety of Jostaki has all the good qualities that are the marked features of the new hybrids of the species. It was selected because of the largeness of its fruit. In this respect it is significantly superior to the variety Josta. Thus, Jostaki is a major amelioration for the cultivation of this new berryfruit variety.

No propagation or other respective material of this variety has been commercialized and there is no known printed and published description of the variety.

The variety, as grown in the Federal Republic of Germany, has the following distinctive marks:

Plant:
- *Shape (longitudinal section).*—Large/round: 1.5 to 2.0 m.

Flower bud:
- *Shape.*—Longish-eggshaped.
- *Position towards shoot.*—Stands off.
- *Size.*—Small to medium: 0.5 to 1.0 cm.

Young shoot:
- *Anthozyan-coloring.*—Missing.
- *Sparkle.*—Strong.
- *Pubescence of the tops.*—Missing or very little.

Leaf:
- *Basic color of the top side.*—Dark green.
- *Sparkle of the top side.*—Strong.

Infructescence:
- *Length.*—Short: 3 to 4 cm.

Fruit:
- *Size.*—Very large: 1.5 to 2.0 cm.
- *Compactness.*—High.
- *Color.*—Black.
- *Taste.*—Sweet-sour with specific flavor.

Time of opening of flower-bud: Early: April 10 to April 20.

Time of beginning of flowering: Early: April 20 to May 10.

Time of fruit maturity: Medium to late: July 15 to July 30.

It is claimed:

1. A new and distinct variety of *Ribes nidigrolaria* named Jostaki and parts thereof as described and illustrated, and particularly characterized by the largeness of the fruit.

* * * * *